United States Patent [19]

Sakurada

[11] 4,260,581

[45] Apr. 7, 1981

[54] AUTOMATIC ANALYSIS APPARATUS

[75] Inventor: Masahiko Sakurada, Machida, Japan

[73] Assignee: Olympus Optical Co., Ltd., Tokyo, Japan

[21] Appl. No.: 117,654

[22] Filed: Feb. 1, 1980

[30] Foreign Application Priority Data

Feb. 7, 1979 [JP] Japan .................................. 54/12324
Feb. 7, 1979 [JP] Japan .................................. 54/12325

[51] Int. Cl.³ .......................... G01N 1/10; G01N 35/04
[52] U.S. Cl. ........................................ 422/65; 422/66; 422/104
[58] Field of Search .................... 422/64, 65, 66, 67, 422/104

[56] References Cited

U.S. PATENT DOCUMENTS

| 3,533,744 | 10/1970 | Unger | 422/65 X |
| 3,728,079 | 4/1973 | Moran | 422/65 |
| 3,843,323 | 10/1974 | Quame | 422/65 X |

Primary Examiner—Ronald Serwin
Attorney, Agent, or Firm—Haseltine and Lake

[57] ABSTRACT

An automatic analysis apparatus which makes use of an exhaustive type reaction vessel, comprising a movable reaction line provided along its overall length with an engage portion operative to be engaged with the reaction vessel, a reaction vessel supply station, a reaction liquid measuring station and a reaction vessel discarding station, all of the stations being arranged along the reaction line in the order as mentioned above.

2 Claims, 5 Drawing Figures

4,260,581

AUTOMATIC ANALYSIS APPARATUS

BACKGROUND OF THE INVENTION

1. Field of the Invention

This invention relates to an automatic analysis apparatus which makes use of an exhaustive type reaction vessel.

2. Description of the Prior Art

In almost all of the above mentioned kind of conventional automatic analysis apparatus, it has been required to detachably mount the reaction vessel and discard the reaction liquid in a manual manner and automation of such manual operation has eagerly been desired. At present, an automatic apparatus in which the above mentioned manual operations are completely automatic has been developed and available in market. In such automatic apparatus, a sample and a reagent are reacted in the reaction vessel and then the reaction liquid is transferred to a decantation member by means of a shifting arm. The decantation member is inclined to pour the reaction liquid into a cuvette, while the vacant reaction vessel is discarded. The reaction liquid in the cuvette is subjected to colorimetric method and then the cuvette is rotated about its horizontal center axis by 180° to discard the reaction liquid. In addition, the vacant cuvette is washed so as to ready for receiving the reaction liquid of the next sample. As seen from the above, the conventional automatic analysis apparatus is relatively complex in construction, and as a result, tends to easily induce the failure and expensive. In addition, the reaction liquid must be transferred into the cuvette that is used repeatedly, so that it is impossible to completely exhibit the merit that use was made of the exhaustive type reaction vessel.

The conventional automatic analysis apparatus which makes use of the exhaustive type reaction vessel has another disadvantage that the reaction vessels are supplied one by one, so that the time lapsed until the reaction vessel arrives at its required reaction temperature becomes long and that it is impossible to precisely maintain the liquid temperature at the reaction temperature thereof by the presence of the heat capacity of the reaction vessel. As a result, the analysis precision could not be improved.

In an automatic analysis apparatus which operative to repeatedly wash and use the reaction vessel, if use is made of hot water for the purpose of washing the reaction vessel, it is possible to maintain the reaction vessel at its desirous temperature. As a result, even in an automatic analysis apparatus which makes use of an exhaustive type reaction vessel whose washing is not necessary, it is conceivable to arrange a heating station along the travelling path of the reaction vessel so as to rise up its temperature to the reaction temperature prior to supply of a given amount of sample and reagent to the reaction vessel. Such construction has the disadvantage that the temperature of the reaction vessel must be changed during the course of the travelling path of the reaction vessel in a relatively short time. As a result, it is difficult to precisely control the temperature of the reaction vessel and hence improve the measurement precision.

SUMMARY OF THE INVENTION

An object of the invention, therefore, is to provide an automatic analysis apparatus which can eliminate the above mentioned drawbacks which have been encountered with the prior art techniques.

A feature of the invention is the provision of an automatic analysis apparatus comprising a movable reaction line provided along its overall length with an engage portion operative to be engaged with an exhaustive type reaction vessel, a supply station arranged at an inlet side of the reaction line and causing the reaction vessels to be engaged with each engage portion of the reaction line one by one, a measuring station arranged at a position succeeding to the inlet side of the reaction line and reacting a given amount of sample and reagent poured in the reaction vessel with each other to produce a reaction liquid and then effecting a required measurement on the reaction liquid, and a discarding station arranged at an outlet side of the reaction line and releasing the reaction vessel from the reaction line and discarding it.

Further objects and features of the invention will be fully understood from the following detailed description with reference to the accompanying drawings, wherein:

DETAILED DESCRIPTION OF THE PREFERRED EMBODIMENTS

Figure 1:
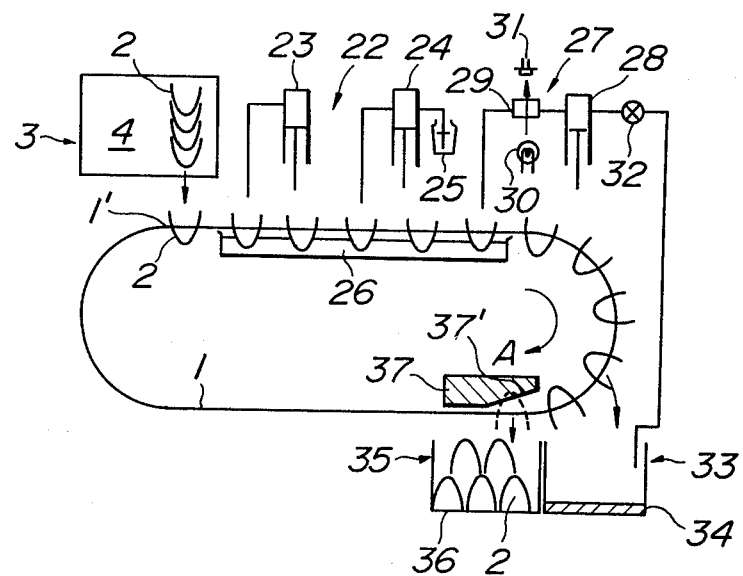
FIG. 1 is a diagrammatic view of one embodiment of an automatic analysis apparatus according to the invention.
Figure 2:
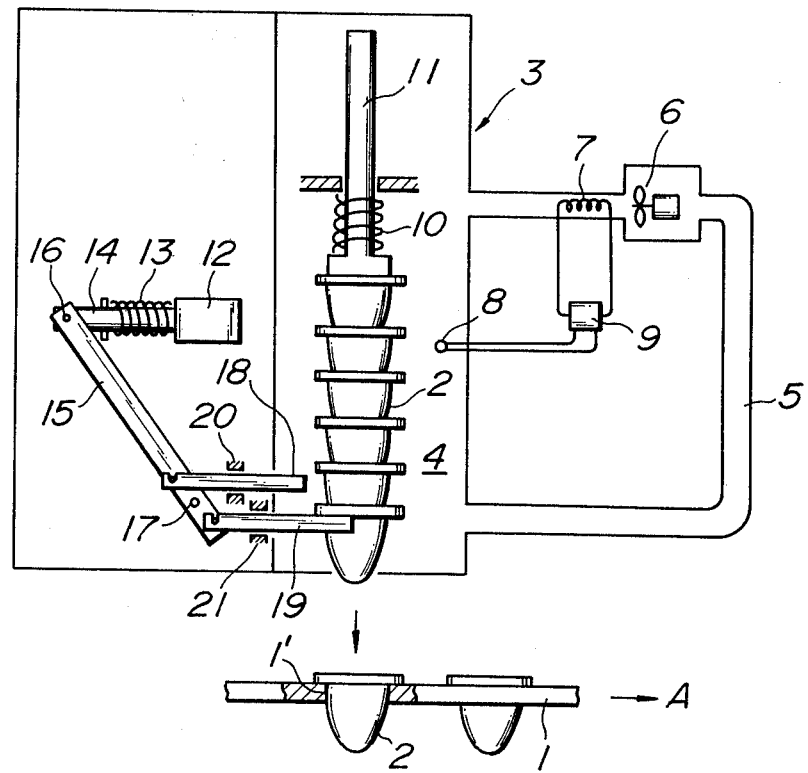
FIG. 2 is a diagrammatic view showing a reaction vessel supply station in detail.

FIG. 1 shows an overall construction of one embodiment of an automatic analysis apparatus according to the invention. In the present embodiment, provision is made of an endless conveyor 1 operative to move in a vertical direction as means for moving an exhaustive reaction vessel 2 in a direction shown by an arrow A along successive stations to be described later. As shown in FIG. 2, the endless conveyor 1 is provided along its total length with a hole 1' engageable with a large diameter portion of the reaction vessel 2 or a flange fitted to the top edge thereof. In the present embodiment, the following stations are arranged along the travelling path of the endless conveyor 1.

(1) A reaction vessel supply station 3.
(2) A given amount of sample and reagent pouring station 22.
(3) A measuring station 27.
(4) A reaction liquid discarding station 33.
(5) A reaction vessel discarding station 35.

The object, construction and operation of these stations will now be described in succession.

The reaction vessel supply station 3:

This station 3 has a number of reaction vessels 2 enclosed therein and superimposed one upon the other. The station 3 is operative to cause the reaction vessel 2 to drop downwardly one by one toward the horizontally travelling portion of the conveyor 1 and make engagement with a hole 1' provided in the conveyor 1. As shown in FIG. 2, the station 3 is provided with a chamber 4 for containing the reaction vessels 2 superimposed one upon the other. The air temperature in the chamber 4 is maintained at a given reaction temperature, usually about 37° C. For this purpose, to the chamber 4 is connected a circulation flow passage 5 in which are arranged a fan 6 and a heater 7. In addition, in the chamber 4 is arranged a temperature sensor 8 whose output is supplied to a control circuit 9 operative to control the amount of heat delivered from the heater 7 to the circulation air, thereby maintaining the reaction vessel at a desirous given temperature.

In the present embodiment, in order to supply the reaction vessel 2 to the endless conveyor 1 by dropping it one by one, the uppermost reaction vessel 2 is pushed downwardly through a push rod 11 by means of a spring 10. In addition, provision is made of a solenoid 12 operative upon receipt of a reaction vessel supply instruction signal. The solenoid 12 is provided with an output member 14 which is normally projected by means of the spring 13. To the free end of the output member 14 is pivoted a link member 15 by means of a pin 16. The link member 15 is rotatably mounted on a pin 17 and those portions of the link member 15 which are located above and below the pin 17 are connected to holding rods 18, 19, respectively, through known pin-oblong hole connection. The holding rods 18, 19 are guided by guide members 20, 21 so as to be displaceable in a horizontal direction, respectively.

If the solenoid 12 is located at its inoperative position shown in FIG. 2 so as to project its output member 14, the front end of the lower holding rod 19 is brought into engagement with the flange provided at the upper edge of the lowermost reaction vessel 2, thereby preventing this reaction vessel 2 from dropping downwardly. If the solenoid 12 receives a reaction vessel supply instruction signal, the solenoid 12 becomes operative to pull the output member 14 thereinto against the spring force of the spring 13, thereby rotating the link member 15 in a clockwise direction about the pin 17. As a result, the front end of the holding rod 18 connected to that portion of the link member 15 which is located above the pin 17 is displaced to the right and becomes engaged with the flange of that reaction vessel located above and next to the lowermost reaction vessel, thereby supporting all of the reaction vessels located above the reaction vessel engaged with the holding rod 18. On the other hand, the front end of the holding rod 19 connected to that portion of the link member 15 which is located below the pin 17 is displaced to the left and separated from the flange of the lowermost reaction vessel, thereby dropping downwardly the lowermost reaction vessel by its own weight.

The given amount of sample and reagent pouring station 22:

This station 22 is composed of a given amount of sample pouring device 23 and a given amount of reagent pouring device 24. The given amount of sample pouring device 23 functions to suck in a given amount of sample from a sample container (not shown) and deliver the sample thus sucked into the reaction vessel 2 moved by means of the conveyor 1. The given amount of reagent pouring device 24 functions to suck in a given amount of reagent from a reagent container 23 and deliver the reagent into that reaction vessel which contains the given amount of sample.

Figure 3:
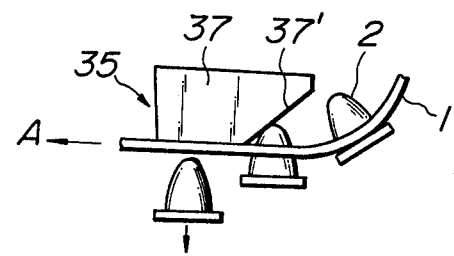
FIG. 3 is a partial view for explaining the operation of a push member arranged at a reaction vessel discarding station.

Provision is made of an elongate constant temperature tank 26 arranged along and beneath the upper side portion of the endless conveyor 1. It is desirous to immerse the reaction vessel 2 into the constant temperature tank 26 and move it under such condition until the reaction liquid produced by the mutual reaction of the given amount of sample and reagent poured into the reaction vessel 2 is sucked into a measuring chamber 29 at a next measuring station 27. The measuring station 27:

This measuring station 27 is composed of a pump 28 for sucking up a portion of the reaction liquid in the reaction vessel 2 and a transparent measuring chamber 29 arranged in a suction flow path extending from the reaction vessel 2 to the pump 28 and interposed between a light emitting element 30 and a light receiving element 31. In the present embodiment, the reaction liquid is subjected to the colorimetric measurement in the transparent measuring chamber 29. After the completion of the measurement, the reaction liquid is fed back into the reaction vessel 2. Alternatively, the reaction liquid may be delivered into a container provided in a reaction liquid discarding station to be described later through a valve 32. In addition, the reaction liquid flow passage inclusive of the measuring chamber 29 may be cleaned by washing so as to prevent the reaction liquid flow passage from being contaminated. The reaction liquid discarding station 33:

This station 33 is composed of a container 34 located at a position below the reaction vessel which has been inclined downwardly at the turning end of the conveyor 1. The reaction liquid in the reaction vessel 2 is spontaneously flowed out thereof in response to the downward inclination of the reaction vessel into the container 34. The reaction vessel discarding station 35:

This station 35 is composed of a recovery box 36 for receiving the reaction vessel 2 dropping downwardly by its own weight from the conveyor 1, the reaction vessel 2 being completely upside down after the reaction liquid has been discarded therefrom. As shown in FIG. 3, provision is made of a push member 37 provided at its one end with a downwardly inclined surface 37' for the purpose of reliably dropping down the reaction vessel from the conveyor 1. The inclined surface 37' is formed such that the base portion of the reaction vessel makes contact with the inclined surface 37' so as to reliably drop downwardly the reaction vessel from the conveyor. At the supply station 3, a new reaction vessel 2 is supplied to and engaged with the hole 1' of the conveyor 1 from which the reaction vessel 2 has been discarded at the station 35.

The automatic analysis apparatus according to the invention has a number of advantages. In the first place, the reaction vessel transfer mechanism is composed of the endless conveyor 1 movable in the vertical surface, so that it is not necessary to provide a reaction vessel detachable mechanism which is complex in construction and a reaction liquid discarding pump. That is, the reaction vessel is dropped and supplied onto the endless conveyor one by one and the reaction liquid is spontaneously flowed out of the reaction vessel at the position of the endless conveyor where the upside thereof becomes down and the reaction vessel is dropped downwardly from the endless conveyor so as to discard it. As a result, it is possible to simplify the construction of the apparatus and improve the reliability of the operation.

Secondly, in the reaction vessel supply station, the reaction vessels are stored under reaction temperature thereof and supplied one by one to the endless conveyor. On the contrary, in the conventional analysis apparatus, the temperature of the reaction vessel is changed from the room temperature to the reaction temperature during the transfer passage of the reaction vessel. As a result, the apparatus according to the invention is not required to consider the rising up temperature of the reaction vessel and hence can be transferred one by one everytime the time required for measuring the reaction liquid and shorter than the rising up time of the reaction vessel is lapsed.

Third, the reaction liquid discarding station and the reaction vessel discarding station are separated from each other, so that the discarded product can simply be treated and recovered contrary to the conventional apparatus in which the reaction liquid and the reaction vessel are discarded into one recovery container.

Fourth, the reaction vessel is formed of a transparent material, so that the colorimetric measurement on the reaction liquid in the reaction vessel can directly be effected, thereby effecting the treatment at a high speed. On the contrary, in the conventional apparatus for effecting colorimetric measurement on the reaction liquid after it has been transferred to the measuring container, the reaction vessel is inclined to flow downwardly the reaction liquid into the measuring container and after completion of the measurement the measuring container is rotated by 180° to discard the reaction liquid. As a result, the required mechanism becomes complex in construction and is not suitable for operating it at a high speed.

Figure 4:
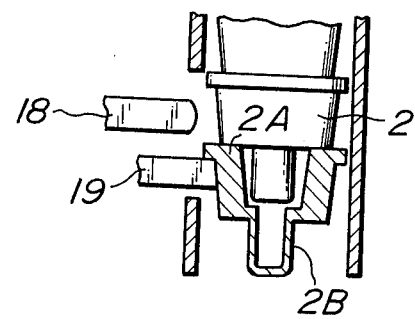
FIGS. 4 and 5 are partial sectional views of modified embodiments of a reaction vessel supply mechanism.
Figure 5:
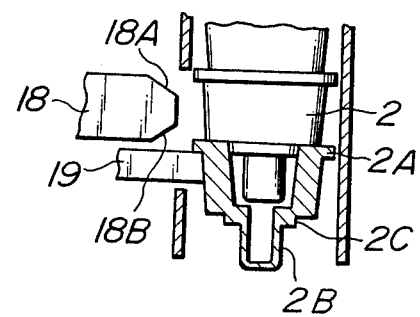

FIGS. 4 and 5 show modified embodiments of the mechanism for dropping downwardly the reaction vessels one by one at the reaction vessel supply station. In the embodiment shown in FIG. 4, holding rods 18, 19 are the same in construction as those shown in FIG. 2, but the reaction vessels 2 are prevented from being closely fitted with each other. That is, the reaction vessel 2 is composed of upper and lower portions 2A and 2B and the other diameter of the lower portion 2B is made smaller than that of the upper portion 2A. As a result, if the holding rod 19 is separated from the lowermost reaction vessel, the lowermost reaction vessel is dropped downwardly without receiving any restraining force from the reaction vessel located above and adjacent to the lowermost reaction vessel.

In the embodiment shown in FIG. 5, the reaction vessel shown in FIG. 4 is provided between the upper portion 2A and the lower portion 2B with a shoulder portion 2C whose outer diameter is made equal to the inner diameter of the upper portion 2A. As a result, it is possible to closely fit each reaction vessel into the next adjacent lower reaction vessel and hence to easily move a number of reaction vessels. But, in the present embodiment, the lowermost reaction vessel could not be separated from the reaction vessel located above and adjacent to the lowermost reaction vessel by its own weight. In order to separate the lowermost reaction vessel from the reaction vessel located above and adjacent to the lowermost reaction vessel, the upper holding rod 18 is provided at its front end with upper and lower inclined surfaces 18A, 18B such that when the upper holding rod 18 is pushed toward the reaction vessel, the upper inclined surface 18A makes contact with the lower surface of the flange provided at the upper portion 2A of the reaction vessel located above and adjacent to the lowermost reaction vessel so as to push up this reaction vessel and at the same time the lower inclined surface 18B makes contact with the upper surface of the flange of the lowermost reaction vessel so as to push down this reaction vessel, thereby separating it from the reaction vessel located above and adjacent to the lowermost reaction vessel and spontaneously dropping it.

Alternatively, provision may be made of a mechanism for forcedly fitting the lowermost reaction vessel into the hole 1' of the endless conveyor 1. Even in this case, the pushing out member 37 shown in FIG. 3 functions to reliably separate the reaction vessel to be discarded from the endless conveyor 1.

The invention is not limited to the above described embodiments only, but various changes and modifications may be made.

What is claimed is:

1. In an automatic analysis apparatus comprising a movable reaction line provided along its overall length with an engage portion operative to be engaged with a disposable reaction vessel, a supply station arranged at an inlet side of said reaction line and causing the reaction vessels to be engaged with each engage portion of said reaction line one by one, a measuring station arranged at a position succeeding to the inlet side of said reaction line and reacting a given amount of sample and reagent poured into the reaction vessel with each other to produce a reaction liquid and then effecting a required measurement on the reaction liquid, and a discarding station arranged at an outlet side of said reaction line and releasing the reaction vessel from said reaction line and discarding it, the improvement in which said supply station is operatively associated with a constant temperature device so as to maintain the reaction vessel at its given temperature.

2. In an automatic analysis apparatus comprising a movable reaction line provided along its overall length with an engage portion operative to be engaged with a discardable reaction vessel, a supply station arranged at an inlet side of said reaction line and causing the reaction vessels to be engaged with each engage portion of said reaction line one by one, a measuring station arranged at a position succeeding to the inlet side of said reaction line and reacting a given amount of sample and reagent poured in the reaction vessel with each other to produce a reaction liquid and then effecting a required measurement on the reaction liquid, and a discarding station arranged at an outlet side of said reaction line and releasing the reaction vessel from said reaction line and discarding it, the improvement in which said discarding station is composed of a first discarding station for discarding the reaction liquid from the reaction vessel and discarding it and a second discarding station for releasing the reaction vessel from the reaction line and discarding it.

* * * * *